US 12,201,479 B2

(12) United States Patent
Hansen

(10) Patent No.: US 12,201,479 B2
(45) Date of Patent: *Jan. 21, 2025

(54) BEAMFORMING IN ULTRASOUND IMAGING SYSTEMS TO CORRECT FOR REFRACTION OF ULTRASOUND BY TRANSDUCER ELEMENTS

(71) Applicant: FUJIFILM SONOSITE, INC., Bothell, WA (US)

(72) Inventor: Michael Hansen, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/491,864

(22) Filed: Oct. 23, 2023

(65) Prior Publication Data

US 2024/0041435 A1 Feb. 8, 2024

Related U.S. Application Data

(63) Continuation of application No. 16/943,959, filed on Jul. 30, 2020, now Pat. No. 11,864,949.

(51) Int. Cl.
*A61B 8/08* (2006.01)
*A61B 8/00* (2006.01)
(52) U.S. Cl.
CPC .......... *A61B 8/5207* (2013.01); *A61B 8/4281* (2013.01); *A61B 8/4494* (2013.01); *A61B 8/488* (2013.01)
(58) Field of Classification Search
CPC .................................................. G01S 7/52049
See application file for complete search history.

(56) References Cited

U.S. PATENT DOCUMENTS

2002/0120196 A1   8/2002   Dubberstein et al.
2002/0173722 A1   11/2002  Hoctor et al.
(Continued)

FOREIGN PATENT DOCUMENTS

| JP | 4711583 B2 | 6/2011 |
| JP | 2017000547 A * | 1/2017 |
| WO | 2020/150253 A1 | 7/2020 |

*Primary Examiner* — Joel Lamprecht
*Assistant Examiner* — Nyrobi Celestine
(74) *Attorney, Agent, or Firm* — Womble Bond Dickinson (US) LLP

(57) ABSTRACT

In one embodiment, a method is provided. The method includes transmitting a set of ultrasound waves to towards a target area. The set of ultrasound waves are transmitted by a set of ultrasound elements. The set of ultrasound elements are positioned at different locations in a transducer assembly. The method also includes receiving a set of reflections of the set of ultrasound waves. The set of reflections of the set of ultrasound waves are received by the set of ultrasound elements. The method further includes determining a set of correction values for the set of ultrasound elements. Each correction value of the set of correction values represents a refraction of one reflection of the set of reflections as the one reflection passes through a respective ultrasound element of the set of ultrasound elements. The method further includes generating imaging data based on the set of reflections of the set of ultrasound waves and the set of correction values for the set of ultrasound elements.

18 Claims, 9 Drawing Sheets

(56) References Cited

U.S. PATENT DOCUMENTS

| | | |
|---|---|---|
| 2004/0039285 A1* | 2/2004 | Ustuner .................. A61B 8/587 600/459 |
| 2013/0079640 A1 | 3/2013 | Osawa |
| 2014/0187953 A1 | 7/2014 | Miyachi et al. |
| 2014/0334266 A1 | 11/2014 | Cogan et al. |
| 2019/0361102 A1 | 11/2019 | Price et al. |

* cited by examiner

BEAMFORMING IN ULTRASOUND IMAGING SYSTEMS TO CORRECT FOR REFRACTION OF ULTRASOUND BY TRANSDUCER ELEMENTS

This application is a continuation of co-pending U.S. application Ser. No. 16/943,959 filed on Jul. 30, 2020, which is incorporated herein by reference.

TECHNICAL FIELD

Aspects of the present disclosure relate to ultrasound imaging systems, and more particularly, to beamforming in ultrasound imaging systems.

BACKGROUND

Transducers, such as acoustic or ultrasound transducers, are used in medical imaging where an acoustic or ultrasound probe transmits and receives ultrasound waves to create images of the internal tissues of a patient. The ultrasound probe may allow a user (e.g., a doctor, clinician, technician, etc.) to view an image of a target area within the body of the patient. The ultrasound probe may use beamforming to generate the image of the target area. Beamforming may refer to the use of multiple sound waves that may interfere with each other constructively and/or destructively. The interference (e.g., constructive interference and/or destructive interference) may allow the ultrasound probe to steer or focus the ultrasound waves at a particular area or focal point.

SUMMARY

In one embodiment, a method is provided. The method includes transmitting a set of ultrasound waves to towards a target area. The set of ultrasound waves are transmitted by a set of ultrasound elements. The set of ultrasound elements are positioned at different locations in a transducer assembly. The method also includes receiving a set of reflections of the set of ultrasound waves, wherein the set of reflections of the set of ultrasound waves are received by the set of ultrasound elements. The method further includes determining a set of correction values for the set of ultrasound elements. Each correction value of the set of correction values represents a refraction of one reflection of the set of reflections as the one reflection passes through a respective ultrasound element of the set of ultrasound elements. The method further includes generating imaging data based on the set of reflections of the set of ultrasound waves and the set of correction values for the set of ultrasound elements.

In one embodiment, an ultrasound probe is provided. The ultrasound probe includes a transducer assembly and a processing device coupled to the transducer assembly. The processing device is configured to transmit a set of ultrasound waves to towards a target area. The set of ultrasound waves are transmitted by a set of ultrasound elements. The set of ultrasound elements are positioned at different locations in the transducer assembly. The processing devices is also configured to receive a set of reflections of the set of ultrasound waves. The set of reflections of the set of ultrasound waves are received by the set of ultrasound elements. The processing device is further configured to determine a set of correction values for the set of ultrasound elements. Each correction value of the set of correction values represents a refraction of one reflection of the set of reflections as the one reflection passes through a respective ultrasound element of the set of ultrasound elements. The processing device is further configured to generate imaging data based on the set of reflections of the set of ultrasound waves and the set of correction values for the set of ultrasound elements.

In one embodiment, an ultrasound imaging system is provided. The ultrasound imaging system includes an ultrasound probe configured to transmit a set of ultrasound waves to towards a target area. The set of ultrasound waves are transmitted by a set of ultrasound elements. The set of ultrasound elements are positioned at different locations in a transducer assembly. The ultrasound probe is also configured to receive a set of reflections of the set of ultrasound waves. The set of reflections of the set of ultrasound waves are received by the set of ultrasound elements. The ultrasound probe is further configured to determine a set of correction values for the set of ultrasound elements. Each correction value of the set of correction values represents a refraction of one reflection of the set of reflections as the one reflection passes through a respective ultrasound element of the set of ultrasound elements. The ultrasound prove is further configured to generate imaging data based on the set of reflections of the set of ultrasound waves and the set of correction values for the set of ultrasound elements. The ultrasound imaging system also includes an imaging system coupled to the ultrasound probe. The imaging system is configured to generate one or more images of the target area based on the imaging data.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

As discussed above, an ultrasound probe may allow a user (e.g., a doctor, clinician, technician, etc.) to view an image of a target area within the body of the patient. The ultrasound probe may use beamforming to generate the image of the target area (e.g., may use multiple ultrasound waves that may interfere with each other constructively and/or destructively). To perform beamforming, an ultrasound probe may combine, sum, etc., the signals (e.g., imaging data) from multiple transducer elements using various weights and/or delays. However, the delays may be affected by refraction of a reflected ultrasound wave as the ultrasound wave travels through a transducer element. Many ultrasound probes may us a random access memory (RAM) to store correction values that should be applied to the delays. The RAM may be an external memory (e.g., double data rate (DDR) RAM). However, RAM is more costly and may increase the complexity of the ultrasound probe (e.g., may us many pins, connections, wires, traces, etc., to access the RAM). Using an external memory may also increase the cost of the ultrasound probe and/or ultrasound imaging system and may also increase the amount of power used by the ultrasound probe and/or ultrasound imaging system.

The implementations, examples, and/or embodiments described herein allow an ultrasound probe and/or an ultrasound imaging system determine, calculate, generate, etc., the correction values while the ultrasound probe is in operation. The ultrasound probe may determine the correction values by generating one or more curves to represent the correction values at different depths. This allows the ultrasound probe to determine the correction values without using RAM (e.g., an external memory) and/or without included RAM within the ultrasound probe. This may reduce the complexity of the ultrasound probe and/or ultrasound imaging system because fewer pins, wires, traces, circuits may be used (e.g., no additional circuits or wires are used to connect to the RAM). This may also reduce the cost of the system and/or may reduce the amount of power used by the ultrasound probe and/or ultrasound imaging system.

Figure 1B:
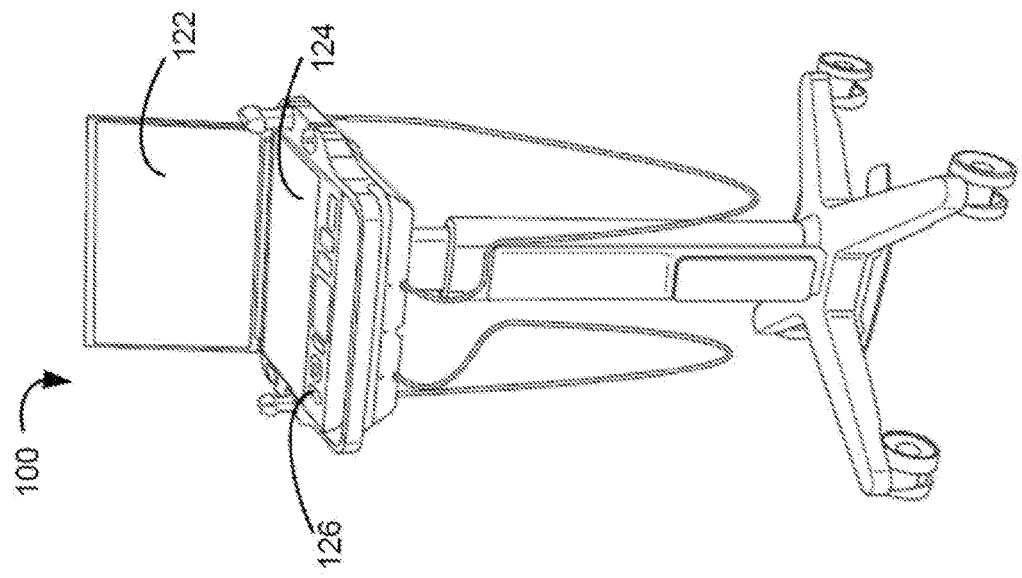
FIG. 1B is an isometric view of an example ultrasound imaging system in accordance with one embodiment of the present disclosure.
Figure 1A:
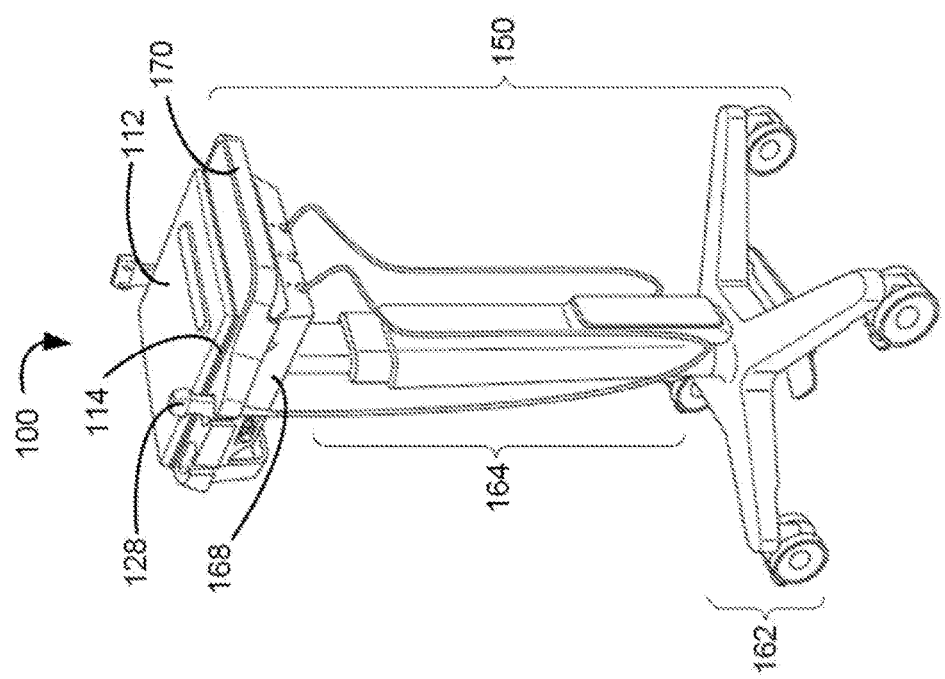
FIG. 1A is an isometric view of an example ultrasound imaging system in accordance with one embodiment of the present disclosure.

FIGS. 1A and 1B show a representative ultrasound imaging system 100 that implements the present technology for detecting fluid movement (e.g., the movement of fluids and/or particles in the fluid) at a target area. In one embodiment, the ultrasound imaging system 100 is a cart-based system that includes an imaging unit removably connected to an adjustable stand. The imaging unit is configured to image human or animal subjects, by sending ultrasound signals or pulses into the target (e.g., the patient's body), receiving reflected echo signals/pulses, and processing the received reflections.

In some embodiments, the imaging unit includes a first interface that is rotatably connected to a second interface, such that a relative angle or orientation between the two interfaces can be changed. For example, in some embodiments, the first and second interfaces are connected through a pin or a hinge joint, such that the first interface and the second interface rotate about an axis corresponding to the joint. In some embodiments, the ultrasound imaging system 100 switches between supported modes according to the relative location, angle, or orientation of the two interfaces. In alternative embodiments, the ultrasound imaging system 100 switches between supported modes according to the relative location, angle, or orientation of one interface with respect to another part of the ultrasound imaging system 100 or a plane defined with respect to the ultrasound imaging system 100, or a part thereof.

In some embodiments, the ultrasound imaging system 100 supports diagnostic imaging modes and one or more procedural modes performed by a medical professional. During a diagnostic examination, the medical professional(s) and/or the operator can use the ultrasound imaging system 100 to passively observe a physiological region of the patient. For example, ultrasound examinations can include one or more of cardiac imaging, abdominal imaging, pelvic imaging, obstetric imaging, Focused Assessment with Sonography in Trauma (FAST) exams, etc.

In comparison, during a procedure, the medical professional(s) and/or the operator uses the ultrasound imaging system 100 to image/track progress while actively performing a medical procedure on a physiological region of the patient to achieve a specific task (e.g., a nerve block). Procedures, in general, can require puncturing of the patient's skin or otherwise inserting a device into the patient's body. Some example examinations and/or procedures can include applications in anesthesiology, angiology, cardiology, emergency medicine, various surgeries, gynecology/obstetrics, otolaryngology, neonatology, ophthalmology, pulmonology, urology, etc. For example, ultrasound-based procedures can include trauma or emergency procedures (e.g., bullet removal or sutures), anesthetic procedures (e.g., perform a nerve block), PICC line procedures, etc.

The ultrasound imaging system 100 is configured to operate in different modes that correspond to the various objectives/scenarios. In some embodiments, the ultrasound imaging system 100 operates in a diagnostics mode and a procedural mode that support one or more diagnostic examinations and one or more procedures, respectively.

In supporting the diagnostic examinations, the ultrasound imaging system 100 operates in a diagnostics mode by target monitoring of the patient's body/tissue. For example, the imaging system processes the received reflections to present a visual depiction of the examined portion of the patient's body. In processing the received reflections, the ultrasound imaging system 100 converts characteristics of the received echo signals (e.g., their amplitude, phase, power, frequency shift, etc.) into data that are quantified and displayed for the user as an image that represents tissue, bone, blood, etc. of the patient's body in the examined region.

In supporting the procedures, the ultrasound imaging system 100 operates in a procedural mode by monitoring the location of medical devices/instruments in relation to the patient's body/tissue. For example, in one embodiment, in the procedural mode, the ultrasound imaging system 100 displays representations of procedural equipment (e.g., needle, stent, catheter/tube, robotic device, etc.) and/or injected material (e.g., contrast, anesthetic, medicine, etc.) relative to an imaged area of the patient's body. Also, in one embodiment, in a procedure mode, the ultrasound imaging system 100 tracks a position, a location, an orientation, etc. of the medical instrument inside a patient's body during the medical procedure.

In some embodiments, a stand for the ultrasound imaging system 100 includes an adjustable hinge configured to facilitate the multiple orientations/positions, and thereby the different operating modes (e.g., diagnostic imaging modes and one or more procedural modes). In at least one embodiment, the adjustable hinge is located in front of a column that supports the imaging unit and/or the docking tray. In one embodiment, the adjustable hinge is further configured to provide different levels of resistance to movement based on a variety of factors, such as a direction of force applied by the operator, a control input from the operator, etc. In one embodiment, the adjustable hinge includes a clutch mechanism configured to provide different levels of resistance according to one or more of a user-operated lever/button, a direction of force or movement, or a combination thereof.

FIG. 1A is an isometric view of a representative ultrasound imaging system 100 in a storage configuration in accordance with an embodiment of the present technology. In some embodiments, the ultrasound imaging system 100 is a conventional clam-shell design with a lid 112 including a display screen (shown closed) and a base portion 114 including processing electronics, power supply, fans, etc. (not shown). The ultrasound imaging system 100 is mounted on a stand 150 with a tilt adjustment as will be explained below. For the storage configuration, the lid 112 can be rotated about a hinge axis and positioned relatively parallel and over the base portion 114. A resulting angle between the two portions can be effectively 0°. In the storage configuration, in one embodiment, the ultrasound imaging system 100 turns off, deactivates, modifies, etc. one or more portions or functionalities thereof, or a combination thereof based on the position and orientation of the imaging system. For example, the ultrasound imaging system 100 turns off or deactivates one or more displays, signal generators, input keys/controllers, software processes, etc.

FIG. 1B is an isometric view of the ultrasound imaging system 100 in a first operating configuration in accordance with an embodiment of the present technology. In some embodiments, the imaging unit includes the lid 112 of FIG. 1A (including e.g., a display screen, a touch screen, etc.) opened with respect to the base portion 114 of FIG. 1A in an operating configuration. The ultrasound imaging system 100 is connected to one or more probes 128 of FIG. 1A that the operator can use to direct ultrasound signals or pulses into the patient's body, and to receive reflected echo signals/pulses. For example, the received reflections are processed to present a visual depiction of the examined portion of the patient's body and/or medical instruments, such as during a diagnostic exam.

In some embodiments, the imaging unit (e.g., the lid 112, the base portion 114, etc.) is attached to the stand 150 of FIG. 1A. The stand 150 includes a column 164 that extends upward from a base 162 (e.g., a wheeled base). The stand 150 further includes a docking tray 168 connected to a top portion of the column 164. The docking tray 168 removably connects to/receives the imaging unit, such as by connecting to and receiving the base portion 114. In some embodiments, the docking tray 168 includes a handle 170 that an operator can grasp to move/displace the ultrasound imaging system 100 and/or orient/position the docking tray 168 and/or the base portion 114.

In some embodiments, an adjustable hinge connects the docking tray 168 to the column 164 and allows the docking tray 168 and a bottom/docked portion of the imaging unit (e.g., the base portion 114 and/or an interface thereon) to rotate relative to a horizontal plane. In one embodiment, the adjustable hinge fixes or holds the docking tray 168 at multiple angles with respect to a horizontal plane. For example, in one embodiment, the adjustable hinge is a barrel-type hinge that includes position stops that limit a range (e.g., between 0-90° below horizontal) of motion/angles for docking tray 168. Other ranges could also be selected based on user/design specifications. For example, in one embodiment, the adjustable hinge includes one or more adjustable motion stops that the user can reposition. Also, in one embodiment, the adjustable hinge includes one or more motion stops that correspond to a specified/designated range of motion. In one embodiment, the hinge has a locking mode (e.g., when a clutch is engaged) that increases the force required to move the hinge so that the imaging system will not change orientation due to gravity, but can easily move to a new orientation if desired. In one embodiment, the hinge includes a button or a lever activated by the weight of the docking tray 168 thereby activating the locking mode. The button or the lever can disengage when the user grabs or lifts the handle 170 or based on the user's manipulation of the clutch mechanism.

To change the operating mode of the imaging system, in one embodiment, the two interfaces are positioned to create an angle in two or more angular ranges. For example, in one embodiment, a medical professional rotates a bottom interface about the horizontal plane to change the operating mode between a diagnostics mode and a procedural mode. To keep the system stable during usage, the column is located behind (i.e., away from the user operating/facing the imaging unit) a center of gravity of the imaging unit and/or the docking tray 168 while adjustable hinge is located below the center of gravity and in front of the column 164. In comparison to having the adjustable hinge co-linear with and directly over the column 164, the above described location of the adjustable hinge increases stability during movement and orientation changes.

In some embodiments, the adjustable hinge includes a clutch mechanism configured to control resistance/friction levels required to move the docking tray 168 and the imaging unit. For example, the clutch mechanism can be configured to provide multiple resistance/friction levels for different directions of movement (e.g., orientation changes of the docking tray 168). The clutch mechanism provides a first resistance level when a user tilts (e.g., rotates about rotational axis of the adjustable hinge) the docking tray 168 upwards, and a second resistance level when the user tilts the docking tray 168 downwards. Also for example, in one embodiment, the clutch mechanism is attached to a control mechanism (e.g., a handle, a lever, a foot pedal, a button, etc.) that is configured to engage and disengage the clutch mechanism according to user manipulation. In one embodiment, the clutch mechanism is configured to provide varying amounts of resistance/friction levels according to the control mechanism, such as force applied thereon or a position thereof. For some embodiments, the clutch mechanism includes a wrap-spring clutch where the tightness of a wound spring can be relieved based on the position of the control mechanism. Further the winding direction provides differing levels of resistance according to different direction (e.g., upward or downward movement at the handle 170) of orientation changes or the direction of the corresponding force. For some embodiments, the clutch mechanism includes a set of plates that are compressed together with differing levels of force according to the control mechanism.

Figure 2:
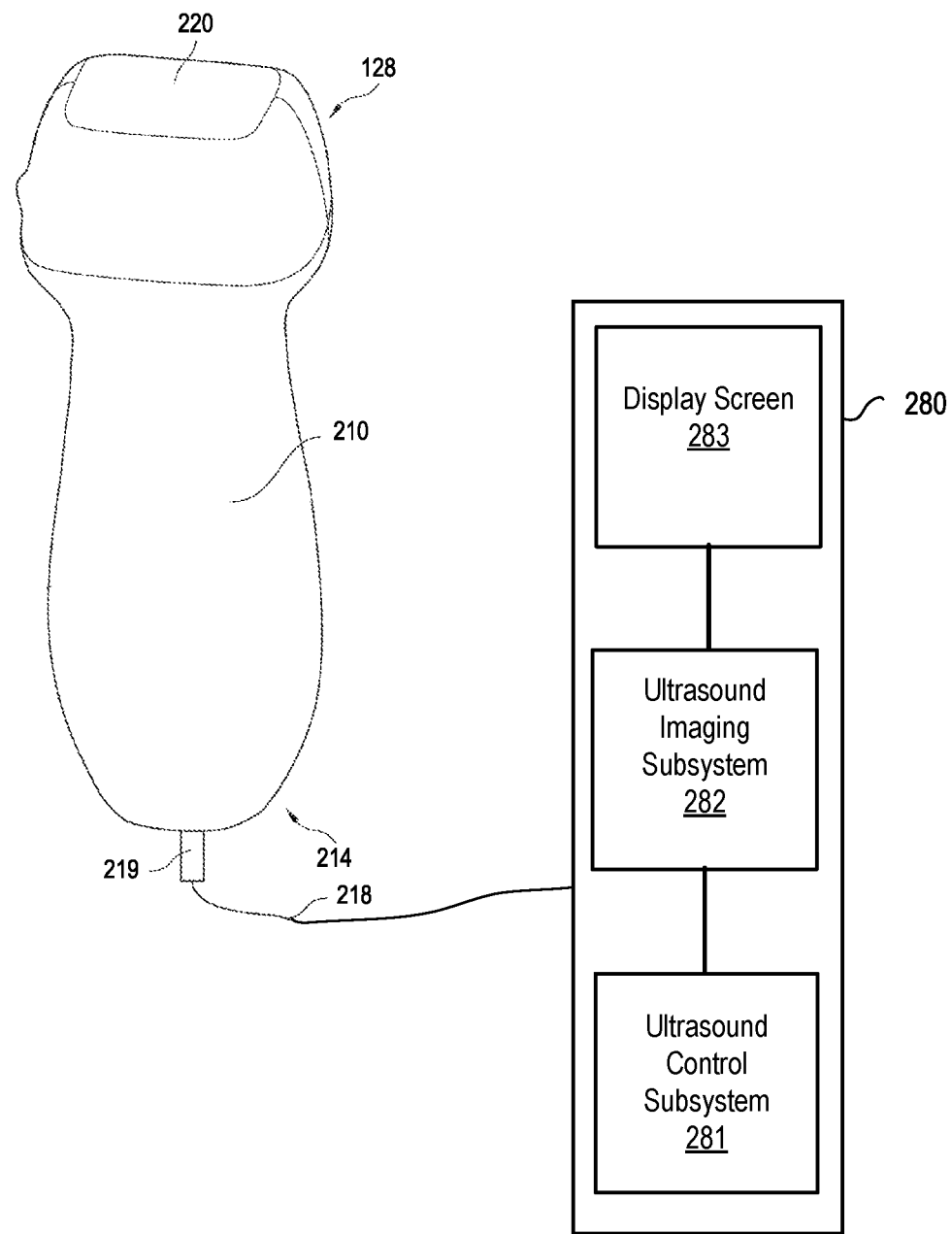
FIG. 2 is a diagram of an example ultrasound imaging system in accordance with one embodiment of the present disclosure.

FIG. 2 illustrates one embodiment of an ultrasound transducer probe having an ultrasound transducer assembly configured in accordance with an embodiment of the disclosed technology. Referring to FIG. 2, ultrasound transducer probe 128 includes an enclosure 210 extending between a distal end portion and a proximal end portion 214. In one embodiment, enclosure 210 of ultrasound transducer probe 128 has a transparent cover that surrounds an inner shell. In one embodiment, the inner shell comprises of metal material (e.g., diecast aluminum, etc.). In one embodiment, the transparent cover comprises transparent plastic (e.g., polysulfone) overmolded on the die cast metal inner shell. In one embodiment, the outer cover and the inner shell create enclosure 210 and work together to transfer heat out of the probe.

Enclosure 210 is configured to carry or house system electronics (e.g., one or more processors, integrated circuits, ASICs, FPGAs, beamformers, batteries and/or other power sources) disposed in an interior portion or cavity of enclosure 210. The system electronics (not shown) are electrically coupled to an ultrasound imaging system 280 via a cable 218 that is attached to the proximal end of the probe by a strain relief element 219.

At the probe tip, a transducer assembly 220 having one or more transducer elements is electrically coupled to the system electronics. In operation, transducer assembly 220 transmits ultrasound energy from the one or more transducer elements toward a subject and receives ultrasound echoes from the subject. The ultrasound echoes are converted into electrical signals by transmit receive circuitry and electrically transmitted to the system electronics and to electronics (e.g., one or more processors, memory modules, beamformers, FPGAs, etc.) in ultrasound imaging system 280 configured to process the electrical signals and form one or more ultrasound images.

Capturing ultrasound data from a subject using an exemplary transducer assembly (e.g., the transducer assembly 220) generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

In one embodiment, ultrasound imaging system 280 includes ultrasound control subsystem 281 having one or more processors. At least one processor causes electrical currents to be sent to the transducer(s) of probe 128 to emit sound waves and also receives the electrical pulses from the probe that were created from the returning echoes. A processor processes the raw data associated with the received electrical pulses and forms an image that is sent to ultrasound imaging subsystem 282, which displays the image on display screen 283. Thus, display screen 283 displays ultrasound images from the ultrasound data processed by the processor of ultrasound control subsystem 281.

In one embodiment, the ultrasound system also has one or more user input devices (e.g., a keyboard, a cursor control device, etc.) that inputs data and allows the taking of measurements from the display of the ultrasound display subsystem, a disk storage device (e.g., hard, floppy, compact disks (CD), digital video discs (DVDs)) for storing the acquired images, and a printer that prints the image from the displayed data (as illustrated in FIGS. 1A and 1B). These also have not been shown in FIG. 2 to avoid obscuring the techniques disclosed herein.

In one embodiment, the ultrasound probe 128 may use beamforming to generate one or more images of a target area. Beamforming may refer to the use of multiple sound waves that may interfere with each other constructively and/or destructively. The interference (e.g., constructive interference and/or destructive interference) may allow the ultrasound probe 128 to steer or focus the ultrasound waves at a particular area or focal point. For example, beamforming may be used to control the interference pattern (e.g., the constructive and/or destructive interference) to focus the amplification of the ultrasound waves at the particular area or focal point. Beamforming may provide various benefits for the ultrasound probe 128. For example, beamforming may improve and/or increase the contrast, spatial resolution, and/or signal-to-noise ration of an ultrasound image. This may allow a user (e.g., a doctor, a clinician, a technician, etc.) to get a better view of a target area (e.g., a focal point).

Figure 3A:
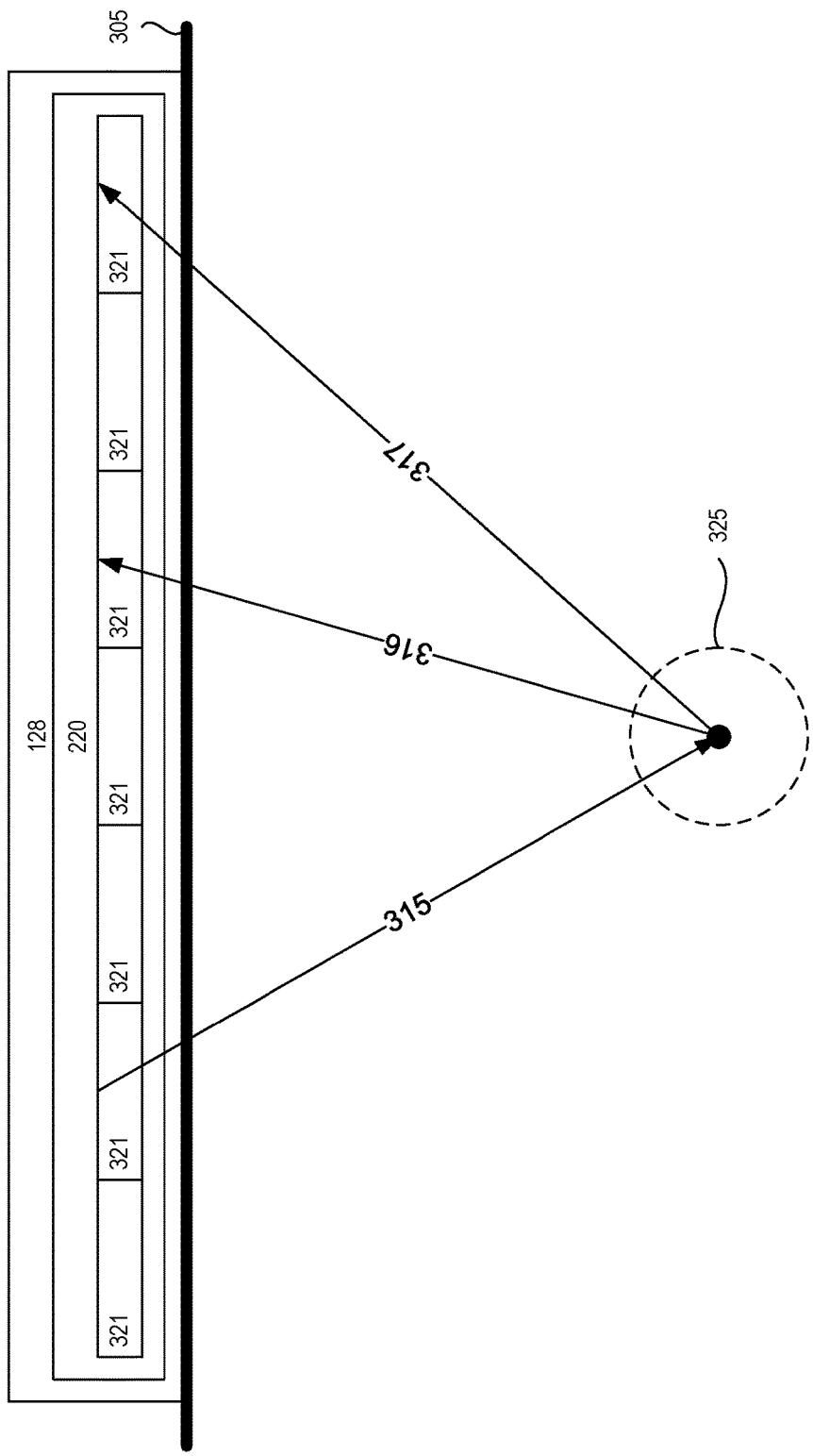
FIG. 3A is a diagram illustrating example ultrasound waves transmitted by an ultrasound probe in accordance with one embodiment of the present disclosure.

FIG. 3A is a diagram illustrating example ultrasound waves 315 transmitted by an ultrasound probe 128 in accordance with one embodiment of the present disclosure. In one embodiment, the ultrasound probe 128 may be able to detect objects, structures, the movement of fluid (e.g., blood, and/or material within the fluid), at a target area underneath the skin 305 (e.g., underneath or within body tissue) of a patient. In one embodiment, the ultrasound probe 128 may use beamforming to generate one or more images of the target area. Beamforming may refer to the use of multiple sound waves that may interfere with each other constructively and/or destructively, as discussed above (e.g., may control the interference pattern to focus the amplification of the ultrasound waves at the particular area or focal point). Beamforming may improve and/or increase the contrast, spatial resolution, and/or signal-to-noise ratio of an ultrasound image. This may allow a user (e.g., a doctor, a clinician, a technician, etc.) to get a better view of the target area 325.

The ultrasound probe 128 includes a transducer assembly 220. The transducer assembly 220 includes multiple transducer elements 321. The transducer elements 321 may be arranged in various different configurations, layouts, etc. For example, the transducer elements 321 may be arranged in a line, or may be arranged in the shape of square/rectangle (e.g., a 2-D array of transducer elements 321). The number of transducer elements 321 may vary in different embodiments. For example, there may be 16, 128, or some other appropriate number of transducer elements 321 in the transducer assembly 220. A transducer element 321 may also be referred to as a lens, a transducer lens, an ultrasound lens, etc.

In one embodiment, the ultrasound probe 128 may transmit ultrasound wave 315 towards the target area 325. For example, one or more of the transducer elements 321 may transmit ultrasound waves towards the target area 325. As illustrated in FIG. 3A, the second transducer element 321 from the left may transmit ultrasound wave 315 towards the target area 325. Although one ultrasound wave 315 is illustrated in FIG. 3A, other transducer elements 321 may transmit additional ultrasound waves to perform beamforming in other embodiments. As the ultrasound wave 315 passes through the target area 325, the ultrasound wave 315 may be reflected back towards the ultrasound probe 128 (e.g., towards the transducer assembly 220 and/or the transducer elements 321). A first reflected ultrasound wave 316 may be received by the fifth transducer element 321 from the left. A second reflected ultrasound wave 317 may be received by the seventh transducer element 321 from the left. Although two reflected ultrasound waves 316 and 317 are illustrated in FIG. 3A, more reflected ultrasound waves may be received by other transducer elements 321 in other embodiments.

Each transducer element 321 may be a different distance from the target area 325 (e.g., from the center of the target area 325). For example, the seventh transducer element 321 from the left is farther away from the target area 325 than the fifth transducer element 321 from the left. The distance between a transducer element 321 and the target area 325 may be determined, calculated, etc., using the Pythagorean theorem (also referred to as the Pythagoras theorem). Because each transducer element 321 may be a different distance from the target area 325, the amount of time for the first reflected ultrasound wave 316 to reach the fifth transducer element 321 from the left may be different from the amount of time for the second reflected ultrasound wave 317 to reach the seventh transducer element 321 from the left (e.g., it may take more time for the second reflected ultrasound wave 317 to reach the seventh transducer element 321 from the left).

As discussed above, the transducer probe 128 may use beamforming to focus the amplification of the ultrasound waves at the target area 325. Because it takes different amount of time for the reflected ultrasound waves to reach different transducer elements 321, the different delays in receiving the reflected ultrasound waves should be accounted for when the transducer probe 128 analyzes, processes, combines, sums, etc., the imaging data that is generated by the transducer element 321. For example, each transducer element 321 may generate a signal when it receives reflected ultrasound waves. The signals generated by the transducer elements 321 may be referred to as imaging data. When the transducer probe 128 receives the different signals from the different transducer elements 321 (which detected the reflected ultrasound waves), the transducer probe 128 may apply different delays to the when summing, combining, etc., the different signals from the different transducer elements 321.

An imaging system (which may be coupled to the ultrasound probe 128, as discussed above) may process the imaging data to generate, provide, present, display, etc., a visual depiction of the target area 325. For example, the imaging system may process the signals generated by the transducer elements 321 to generate one or more images of the target area 325. Because the different signals (e.g., imaging data) from the transducer elements 321 may be summed or combined to generate the images of the target area 325, determining accurate delays for each of the reflected ultrasound waves may be useful and/or important. For example, determining accurate delays for each of the reflected ultrasound waves may allow the ultrasound probe 128 to generate images of the target area 325 with fewer errors.

Figure 3B:
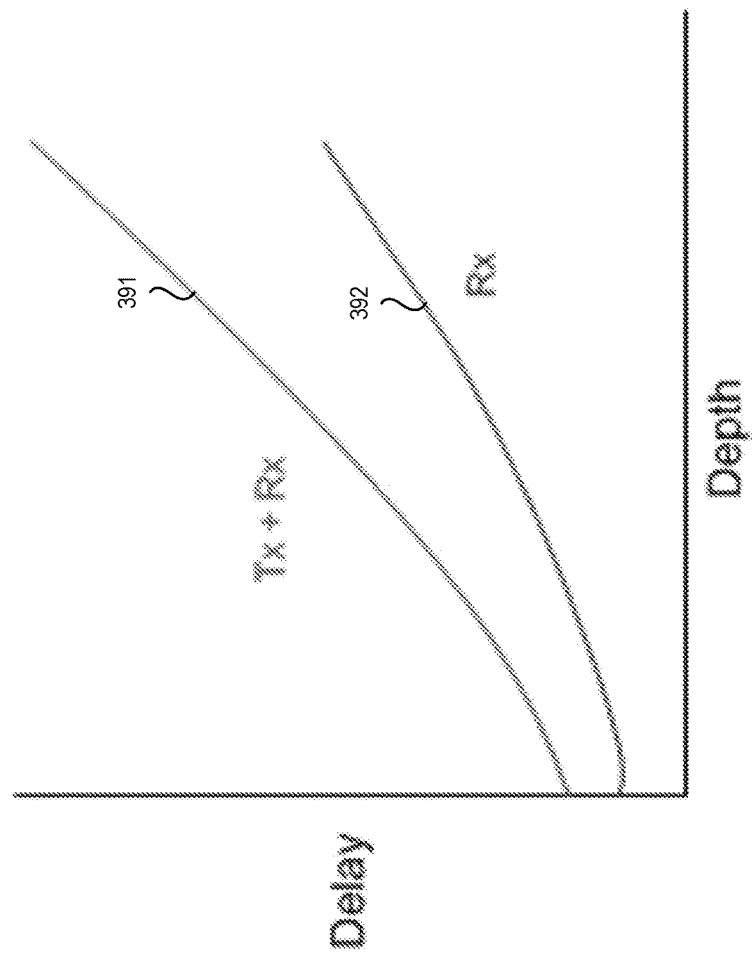
FIG. 3B is an example graph illustrating example delays in receiving reflected ultrasound waves in accordance with one embodiment of the present disclosure.

FIG. 3B is an example graph 390 illustrating example delays (e.g., delay values) in receiving reflected ultrasound waves in accordance with one embodiment of the present disclosure. The graph 390 illustrates the amount of delay (e.g., the time) it takes for an ultrasound wave to be transmitted to a target area and reflected back towards a particular transducer element. The X-axis of the graph 390 represents the depth of the target area. The Y-axis of the graph 390 represents the amount of time it may take for an ultrasound wave to be reflected back to the particular transducer element.

Line 391 illustrates the delay (e.g., the amount of time) it takes for a transmitted ultrasound wave to reach a target area and reflected back to the particular transducer element (e.g., the time for the ultrasound wave to reach the target area and for the reflected ultrasound wave to reach the particular transducer element). Line 392 illustrate the amount of time for an ultrasound wave to be reflected back to the particular transducer element (e.g., the time for the reflected ultrasound wave to reach the particular transducer element from the target area). The time it takes for the transmitted ultrasound wave to reach the target area may be determined or calculated by taking the difference between the line 391 and the line 392 at the depth of the target area.

Figure 4A:
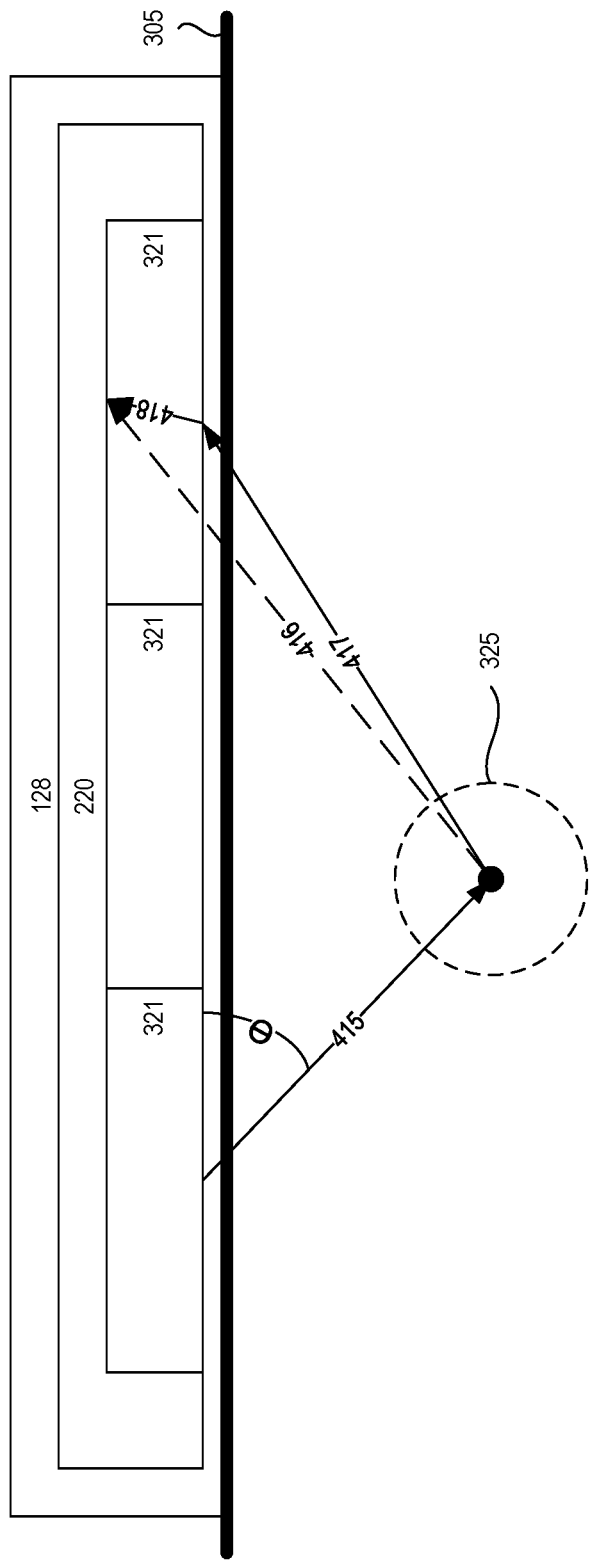
FIG. 4A is a diagram illustrating example ultrasound waves transmitted by an ultrasound probe in accordance with one embodiment of the present disclosure.

FIG. 4A is a diagram illustrating example reflected ultrasound waves that may be received by an ultrasound probe 128 in accordance with one embodiment of the present disclosure. The ultrasound probe 128 includes a transducer assembly 220. The transducer assembly 220 includes multiple transducer elements 321. The transducer elements 321 may be arranged in various different configurations, layouts, etc. The number of transducer elements 321 may vary in different embodiments. In one embodiment, the ultrasound probe 128 may use beamforming to generate one or more images of the target area (e.g., may use of multiple sound waves that may interfere with each other constructively and/or destructively. Beamforming may improve and/or increase the contrast, spatial resolution, and/or signal-to-noise ration of an ultrasound image. This may allow a user (e.g., a doctor, a clinician, a technician, etc.) to get a better view of the target area 325.

As discussed above, the transducer probe 128 may use beamforming to focus the amplification of the ultrasound waves at the target area 325. Because it takes different amount of time for the reflected ultrasound waves to reach different transducer elements 321, the different delays in receiving the reflected ultrasound waves should be accounted for when the transducer probe 128 analyzes, processes, combines, sums, etc., the imaging data (e.g., one or more signals) that is generated by the transducer element 321. When the transducer probe 128 receives the different signals from the different transducer elements 321 (which detected the reflected ultrasound waves), the transducer probe 128 may apply different delays to the when summing, combining, etc., the different signals from the different transducer elements 321.

Because the different signals (e.g., imaging data) from the transducer elements 321 may be summed or combined to generate the images of the target area 325, determining accurate delays for each of the reflected ultrasound waves may be useful and/or important. As discussed above, the ultrasound probe 128 may transmit ultrasound wave towards the target area 325 along the path indicated by line 415. Line 415 may be referred to as a focal line. As the ultrasound wave passes through the target area 325, the ultrasound wave may be reflected back towards the ultrasound probe 128 (e.g., towards the transducer assembly 220 and/or the transducer elements 321).

Line 416 may represent a direct path from the target area 325 towards the transducer element 321 (e.g., the middle transducer element 321). The length of the line 416 may be referred to as D. However, the reflected ultrasound wave (e.g., an ultrasound wave) may not travel along the path illustrated by line 416. Instead, the reflected ultrasound wave may travel along the path indicted by lines 417 and 418. Line 417 may indicate the path of the reflected ultrasound wave as the reflected ultrasound wave travels through a first medium (e.g., a human body, body tissue, etc.). The length of the line 417 may be referred to as M. As the reflected ultrasound wave reaches the transducer element 321 and pass through the transducer element 321, the path and/or direction of the reflected ultrasound wave may change. Line 418 may indicate the path of the reflected ultrasound wave as the reflected ultrasound wave travels through the transducer element 321 (e.g., a second medium). This change in the path of the reflected ultrasound wave may be referred to as refraction, lens refraction, etc. The length of the line 418 may be referred to as L.

As illustrated in FIG. 4A, the total length of the lines 417 and 418 is longer than the length of line 416. Thus, the reflected ultrasound may take additional time to travel through the transducer element 321 along lines 417 and 418, when compared to line 416. As discussed above, the different delays in receiving the reflected ultrasound waves should be accounted for when the transducer probe 128 analyzes, processes, combines, sums, etc., the imaging data (e.g., signal) that is generated by the transducer element 321. The transducer probe 128 may be able to generate more accurate images of the target area if the additional delay caused by the refraction is accounted for when combining the signals generated by the transducer elements 321.

As illustrated in FIG. 4A, the distance traveled by the reflected ultrasound wave is L+M. However, ultrasound probes may generally use the distance D to represent the distance travelled by the reflected ultrasound wave. Thus, the extra distance traveled by the reflected ultrasound wave (due to refraction) may be represented as L+M−D. This additional delay caused by the refraction of the reflected ultrasound wave may have more of an effect on beamforming in the near field of the ultrasound probe. For example, the additional delay may be larger for ultrasound waves reflected from areas closer to the transducer probe 128. The additional delay may be accounted for by using correction values when performing beamforming, as discussed in more detail below.

In one embodiment, the ultrasound probe 128 may transmit a set of ultrasound waves (e.g., one or more ultrasound waves) towards the target area. The set of ultrasound waves may be transmitted by one or more transducer elements 321. As discussed above, the transducer elements 321 may be positioned at different locations in the transducer assembly 220 (e.g., the transducer elements may be laid out in a 2-D array). One or more of the transducer elements 321 may receive reflections of the set of ultrasound waves (e.g., a set of reflected ultrasound waves). The ultrasound probe 128 may receive a set of reflections of the set of ultrasound waves. For example, one or more transducer elements 321 may receive reflected ultrasound waves that are reflected back towards the ultrasound probe 128 from the target area 325.

In one embodiment, the ultrasound probe 128 may determine a set of correction values for the set of transducer elements 321. Each correction value may be used to represent or account for the refraction of a reflected ultrasound wave as the reflected ultrasound wave passes through a respective transducer element 321. For example, each correction value may represent a delay (e.g., an additional delay) that should be applied to the signals (e.g., imaging data) generated by the transducer element 321 when the transducer element 321 receives the reflected ultrasound wave. Each correction value may represent, model, indicate, etc., the refraction of the reflected ultrasound wave as the reflected ultrasound wave travels through a respective transducer element 321. In one embodiment, a correction value may be a delay (e.g., a time) that should be used when the transducer probe 128 (e.g., a circuit, FPGA, ASIC, or other processing device of the transducer probe 128) combines the signal (e.g., imaging data) generated by the transducer element 321 with other signals (e.g., other imaging data) generated by other transducer elements 321. For example, the correction value may be a time (e.g., in milliseconds, microseconds, etc.) that is used when the transducer probe combines the signal generated by the transducer element 321 with other signals generated by other transducer elements 321.

In one embodiment, an imaging system (e.g., ultrasound imaging system 280 illustrated in FIG. 2) may generate one or more images of the target area 325 based on the imaging data. For example, the imaging system may generate multiple images, a video, etc., based on the imaging data and may present the images and/or video to a user via a display (e.g., a screen, a LCD, etc.). In one embodiment, the transducer probe 128 may generate one or more images of the target area 325 based on the imaging data and may provide the images to a display.

In one embodiment, the correction value may be based on the angle at which the set of ultrasound waves are transmitted to the target area 325. For example, line 415 illustrates the path of an ultrasound wave transmitted by the leftmost transducer element 321. As illustrated in FIG. 4A, the line 415 is oriented at an angle θ relative to the skin 305 and the target area 325. Thus, the ultrasound wave may be transmitted at the angle θ. The angle θ may be referred to as the scan angle. The angle θ may be used by the transducer probe 128 identify, determine, select, calculate, generate, etc., a curve. The curve may be used to determine the appropriate delay that should be used for a particular transducer element 321, as discussed in more detail below.

In one embodiment, the correction value for a transducer element 321 may be based on the location of the transducer element 321 within the transducer assembly 220. For example, the correction value may be larger for the leftmost (or rightmost) transducer element 321 of the transducer assembly 220, than for a transducer element 321 that is located in the center of the transducer assembly 220.

In one embodiment, the correction values may be based on the type of operation that the transducer probe 128 is performing. For example, the correction values may be based on the type of examination that is being performed by a clinician, technician, doctor, etc. In another example, the correction values may be based on whether the transducer probe 128 is generating images for the near field or far field. Compensating for lens refraction using the correction values may have a larger impact in the near field because of the angles of the ultrasound waves and the lens refraction, and the shorter distance to the target area. For example, examinations of shallow physiology, such as pediatric vascular access, superficial nerves, musculo-skeletal (MSK) examinations, superficial peripheral vascular access, etc., may benefit more from lens refraction compensation.

Figure 4B:
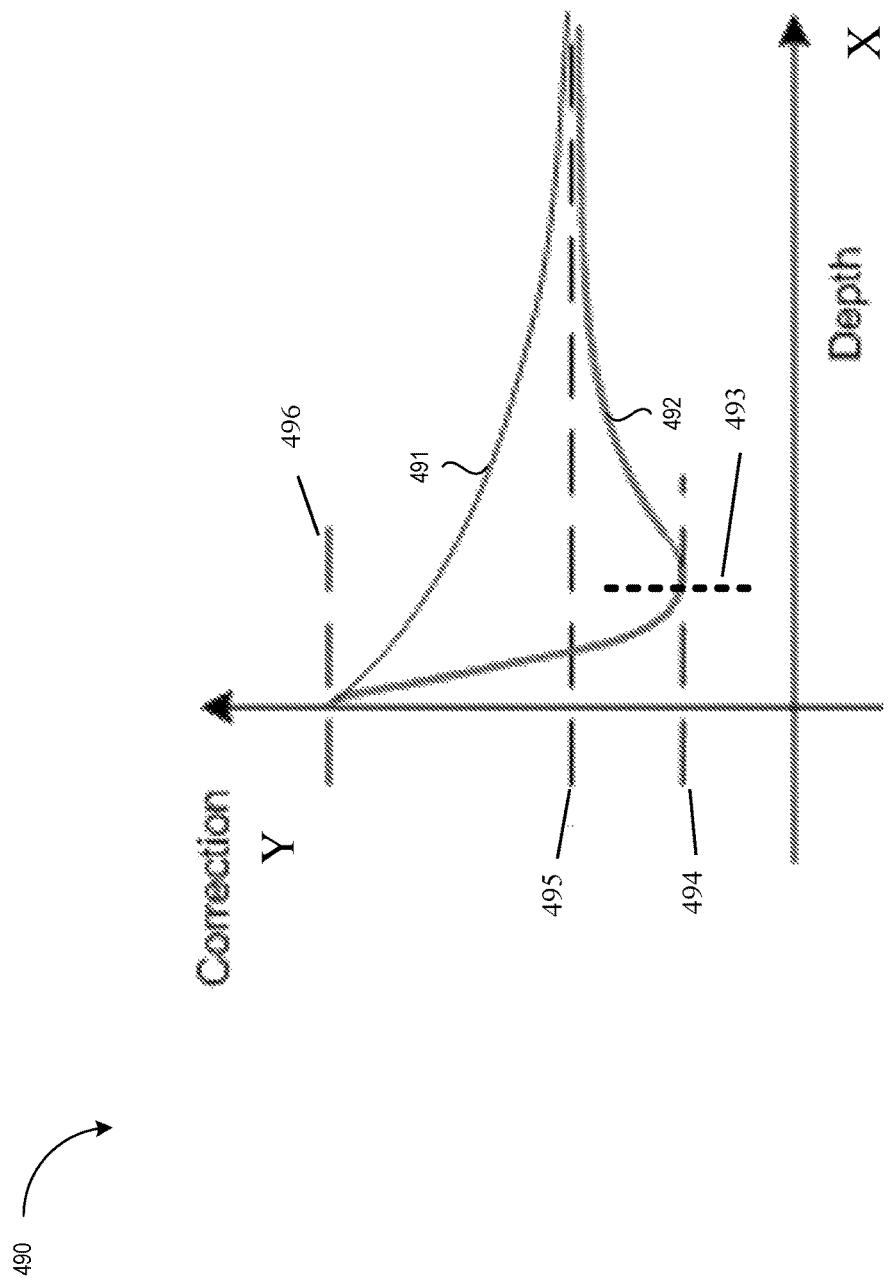
FIG. 4B is an example graph illustrating example corrections that may be used when in receiving reflected ultrasound waves in accordance with one embodiment of the present disclosure.

In one embodiment, the transducer probe 128 may use one or more curves to determine, generate, calculate, etc., correction values for a transducer element 321. The transducer may determine, calculate, generate, obtain, etc., one or more curves. The curves may indicate the correction that may be applied/used when the target area is at different depths, as illustrated in FIG. 4B.

In one embodiment, one curve may be used to indicate, determine, obtain, etc., correction values for one or more transducer elements 321. For example, one curve may be used to obtain correction values for a first set of transducer elements 321 (e.g., to determine a delay for the first set of transducer elements 321 based on the depth of the target area 325). A second curve may be used to obtain correction values for a second set of transducer elements 321 (e.g., to determine a delay for the second set of transducer elements 321 based on the depth of the target area 325).

In one embodiment, the one or more curves may be determined (e.g., generated, calculated, obtained, etc.) based on the angle at which the set of ultrasound waves are transmitted to the target area 325 (e.g., the scan angle). For example, there may be multiple types or shapes of curves. The transducer probe 128 may identify or select one of the types/shapes of curves based on the angle θ illustrated in FIG. 4A. In another example, the slope of different portions of the curve may be based on the angle θ illustrated in FIG. 4A (e.g., the slope may be larger at the left side of the curve and may decrease as the curve goes towards the right). The transducer probe 128 may generate the curve (with varying slopes at different points in the curve) based on the angle θ.

In one embodiment, the transducer probe 128 may generate the curve by generating multiple portions (e.g., pieces, fragments, parts, sections, segments, etc.) of the curve and combining the multiple portions to form the curve. Each of the portions may be linear segments (e.g., lines). Curves that are formed or generated by combining multiple portions (e.g., multiple lines) may be referred to as piecewise linear curves. A piecewise linear curve may be an approximation of a curve function (which may generate a curve that is similar in shape to the piecewise linear curve).

In one embodiment, the transducer probe 128 may include one component (e.g., a circuit, hardware, an FPGA, logic, etc.) that may be used to generate the different portions of a curve (e.g., a piecewise linear curve that may be used to determine a correction value). The one component (e.g., a correction component) may be used to generate the portions for multiple curves. In another embodiment, the transducer probe 128 may include multiple components (e.g., multiple circuits, hardware, FPGAs, etc.) that may be used to generate portions for different curves. For example, each there may be one component for each transducer element 321 (e.g., one correction component for each transducer element 321) and each component may generate portions of a curve for the transducer element 321. In another example, there may be multiple components and each of the multiple components may be shared by multiple transducer elements 321 (e.g., each of the multiple correction components may generate curves that may be used for multiple transducer elements 321).

In one embodiment, the transducer probe 128 may determine the correction values for the one or more transducer elements 321 while the transducer probe 128 is in operation. For example, the transducer probe 128 may determine the correction values that should be applied to the signals generated by the transducer elements 321 as the transducer probe 128 transmits (e.g., emits, generates, etc.) ultrasound waves. In another example, the transducer probe 128 may generate, calculate, determine, obtain, etc., curves (which indicate the correction values at different depths) while the transducer probe 128 transmits ultrasound waves. This may be referred to as determining the correction values on the fly.

Generally, correction values may be pre-computed (e.g., computed, determined, calculated, etc., in advance) and stored in a random access memory (RAM), such as double data rate (DDR) RAM. However, RAM (e.g., DDR RAM) may be a more expensive component and may also use more power. RAM may also use more pins or connections to allow the transducer probe 128 to access the RAM (e.g., to read the correction values) which may increase the complexity of the hardware (e.g., circuits, pins, connections, boards, layouts, etc.) in the ultrasound imaging system. In addition, the RAM may not be located within the transducer probe 128 but may be included in a computing device that is coupled to the transducer probe 128 (e.g., may be located in the ultrasound control subsystem 281 illustrated in FIG. 2). This may increase the time (e.g., latency) to access the correction values and use them when performing beamforming.

The embodiments, implementations, and/or examples, allow the transducer probe 128 to generate, compute, obtain, etc., correction values during the operation of the transducer probe 128. For example, the transducer probe 128 may determine, generate, calculate, etc., a curve (e.g., a piecewise linear curve) that may indicate correction values for a transducer element 321 at different depths. The transducer probe 128 may use the curve to determine a correction value (e.g., a delay, a time, etc.) that should be used when combining imaging data (e.g., signals) from multiple transducer elements 321. This allows the transducer probe 128 to quickly determine a correction value while the transducer probe 128 is in operation. In addition, this allows the transducer probe 128 to perform the beamforming without using RAM (which may use more power and increase the complexity of the transducer probe 128). For example, the transducer probe 128 may lack RAM (e.g., may not have RAM). The transducer probe 128 may determine the correction values while the transducer probe 128 is in operation rather than using pre-computed or pre-calculated delay values stored in a RAM.

FIG. 4B is an example graph 490 illustrating example corrections that may be used when in receiving reflected ultrasound waves in accordance with one embodiment of the present disclosure. The graph 490 illustrates the correction value (e.g., the time or delay that should be added) for target areas at different depth. The X-axis of the graph 490 represents the depth of a target area. The Y-axis of the graph 490 represents the correction value that should be applied to a particular transducer element.

The graph 490 includes curve 491 and 492. The curves 491 and 491 each indicate correction values (e.g., delays, times, etc.) for target areas at different depths. In one embodiment, the curve 491 may indicate the correction values that may be used to account for refraction (e.g., lens refraction) when the angle of the transmitted ultrasound waves is between a threshold range of angles. For example, the curve 491 may indicate the correction values that may be used when the ultrasound waves are transmitted at an angle between 70° to 110°. The curve 492 may indicate the correction values that may be used to account for refraction when the angle of the transmitted ultrasound waves is outside of a threshold range of angles. For example, the curve 492 may indicate the correction values that may be used when the ultrasound waves are transmitted at an angle between 0° to 69° or between 111° to 180°.

In one embodiment, if the ultrasound waves are transmitted at an angle that is less than 90 degrees, curve 491 may be applied to (or used by) receive elements 321 to the right of the transmit origin of line 415 and curve 492 may be applied to (or used by) to receive elements 321 to the left. If the ultrasound waves are transmitted at an angle that is more than 90 degrees, curve 491 may be applied to (or used by) receive elements 321 to the left of the transmit origin of line 415 and curve 492 may be applied to (or used by) receive elements 321 to the right of the transmit origin of line 415. For example, curve 491 may be applied to and/or used by elements on the side of the transmit origin that the line 415 points to and curve 492 may be applied to and/or used by elements on the opposite side.

In one embodiment, a correction value may be used in conjunction with the delays illustrated in FIG. 3B. For example, a delay (delay value) for a particular transducer element may be determined, calculated, generated, obtained, etc. The correction value may be added to the delay to obtain a corrected delay (e.g., a corrected delay value). The corrected delay value may be used by the ultrasound probe to combine, sum, etc., the imaging data (e.g., signals) that are generated by the transducer elements in the transducer assembly 220.

As discussed above, a curve may be obtained by generating multiple portions, pieces, segments, of the curve. For example, the curve 492 may be divided into two portions. The first portion of the curve 492 may be to the left of the vertical dotted line 493. The second portion of the curve 492 may be to the right of the vertical dotted line 493. As shown in FIG. 4B, for curve 492, the correction value decreases from horizontal dotted line 496 as the depth increases to vertical dotted line 493. As shown in FIG. 4B, for curve 492, the correction value increases from horizontal dotted line 494 to horizontal dotted line 495 as the depth increases from vertical dotted line 493. As shown in FIG. 4B, for curve 491, the correction value decreases from horizontal dotted line 496 to horizontal dotted line 495 as the depth increases. Various parameters, criteria, variables, etc., may be used to generate a curve and/or portions (e.g., pieces, segments, etc.) of the curve. For example, one or more of the spacing between the elements (e.g., transmit/receive elements) of the ultrasound probe head, the number of elements in the ultrasound probe head, the location of the element that is transmitting, the transmit rate (e.g., the number of pings or waves transmitted per second or other period of time), the angle of the transmitted waves (e.g., the steering angle), etc., may be used as parameters or factors when generating the curves and/or portions of the curves. Other parameters may include one or more of the refraction index of body tissue, the refraction index of the elements (e.g., the lens), other lens refraction parameters, etc.

In one embodiment, the ultrasound probe (e.g., beamforming component 506, correction component 530, delay component 520, etc.) may calculate, generate, or determine the curves and/or portions of the curve (e.g., piecewise linear (PWL) curves). For example, the ultrasound probe may generate the curve based one or more formulas/equations (e.g., a polynomial equation, a quadratic equation, etc.) and/or based on the parameters discussed above. In another embodiment, the ultrasound probe may use the parameters to identify different portions of curves (e.g., PWL curves) that can be combined to form the curve that will be used by or applied to an element. For example, the ultrasound probe may store different PWL curves and the different PWL curves may be associated with different parameters (e.g., number of elements, element spacing, refraction index, etc., as discussed above). The ultrasound probe may select different PWL curves and combine them together to form the final curve that may be used by or applied to an element.

Although two types (e.g., shapes) of curves are illustrated in FIG. 4B, in other embodiments, more types of curves may be used. Additional curves may be used to determine the correction values for additional ranges of angels. For example, if there are three ranges of angles, three curves may be used. Each of the three curves may have different shapes (E.g., different slopes and/or changes in slope at different locations along the curve).

Figure 5:
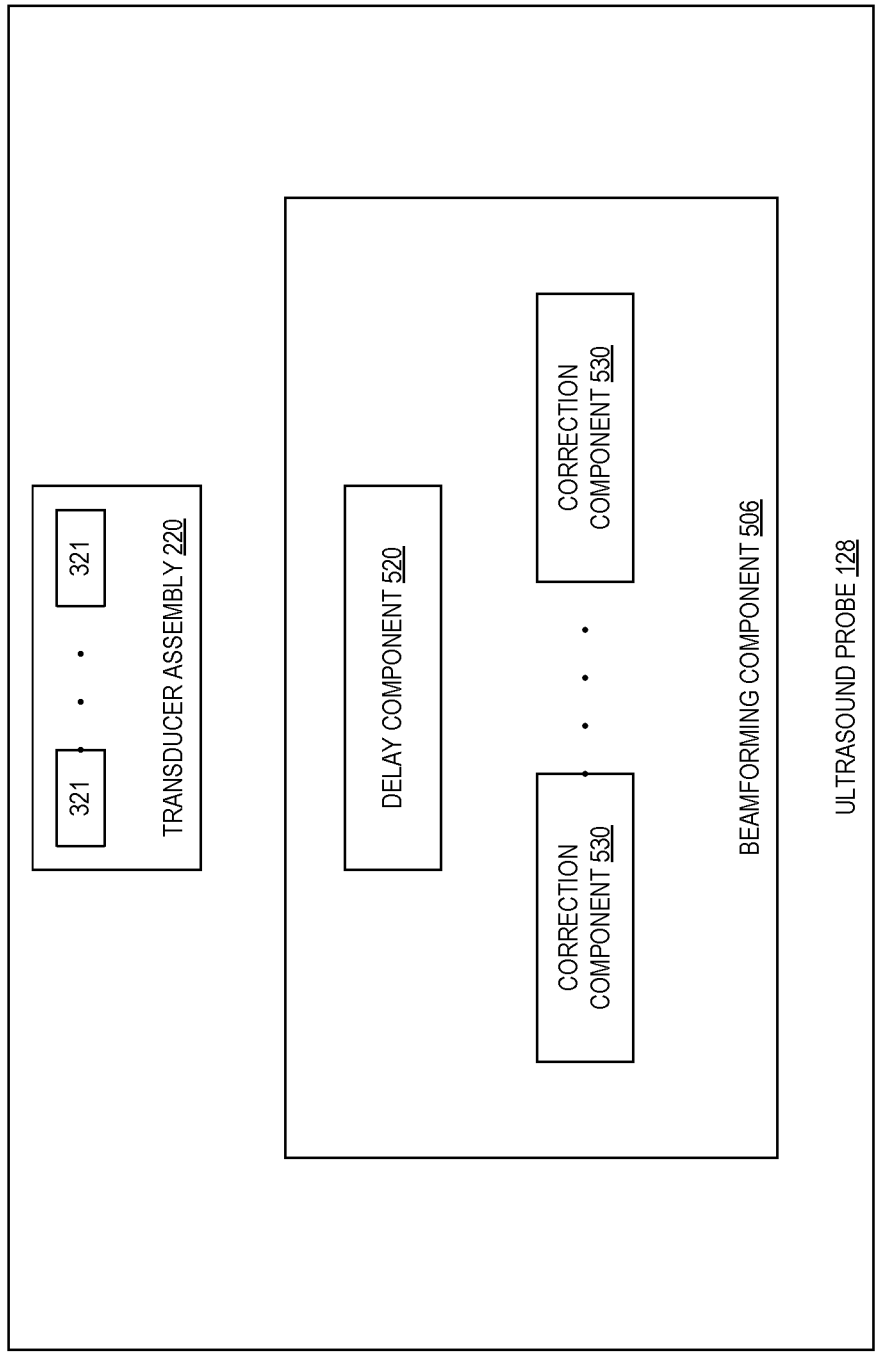
FIG. 5 is a diagram illustrating an example ultrasound probe in accordance with one embodiment of the disclosure.

FIG. 5 is a diagram illustrating an example ultrasound probe 128 in accordance with one embodiment of the disclosure. The ultrasound probe 128 includes a transducer assembly 220, a beamforming component 506. The transducer assembly includes one or more transducer elements 321. The beamforming component 506 includes a delay component 520 and one or more correction components 530. Each of the detection component 505, the beamforming component 506, and the one or more correction components 530 may be hardware (e.g., a circuit, a processing device, a processor, a processing core, an FPGA, an ASIC, etc.), software (e.g., an application, a service, etc.), firmware, or a combination thereof. In one embodiment, there may be one correction component 530 for each transducer element 321 in the transducer assembly 220. For example, if there are 64 transducer element 321, there may be 64 correction components 530.

As illustrated in FIG. 5, the ultrasound probe 128 also includes a beamforming component 506. The beamforming component 506 may perform weighting and summing of the imaging data (e.g., signals) representing the reflections of the ultrasound waves (e.g., reflected ultrasound waves) detected by the transducer assembly 220. The beamforming component 506 may allow the transducer probe 128 to compensate for delays due to the position of transducer elements 321 within the transducer assembly 220.

The delay component 520 may determine different delays (e.g., delay values) that should be applied to different signals generated by different transducer elements. For example, the delay component 520 may determine delay values as illustrated in the line 391 illustrated in FIG. 3B. The correction components 530 may determine one or more correction values which should be used when combining the different signals (e.g., imaging data) generated by the different transducer elements 321. For example, the correction components 530 may generate curves (e.g., PWL curves), pieces of curves, and may determine a correction value based on the curves, as discussed above. The correction components 530 may also identify different PWL curves (e.g., preloaded or previously saved PWL curves) and combine them to form the curve that will be applied or used for different elements. The correction components 350 may provide the correction values to the delay component 520 and the delay component 520 may use the correction values to perform weighting and summing of the imaging data (e.g., signals).

Figure 6:
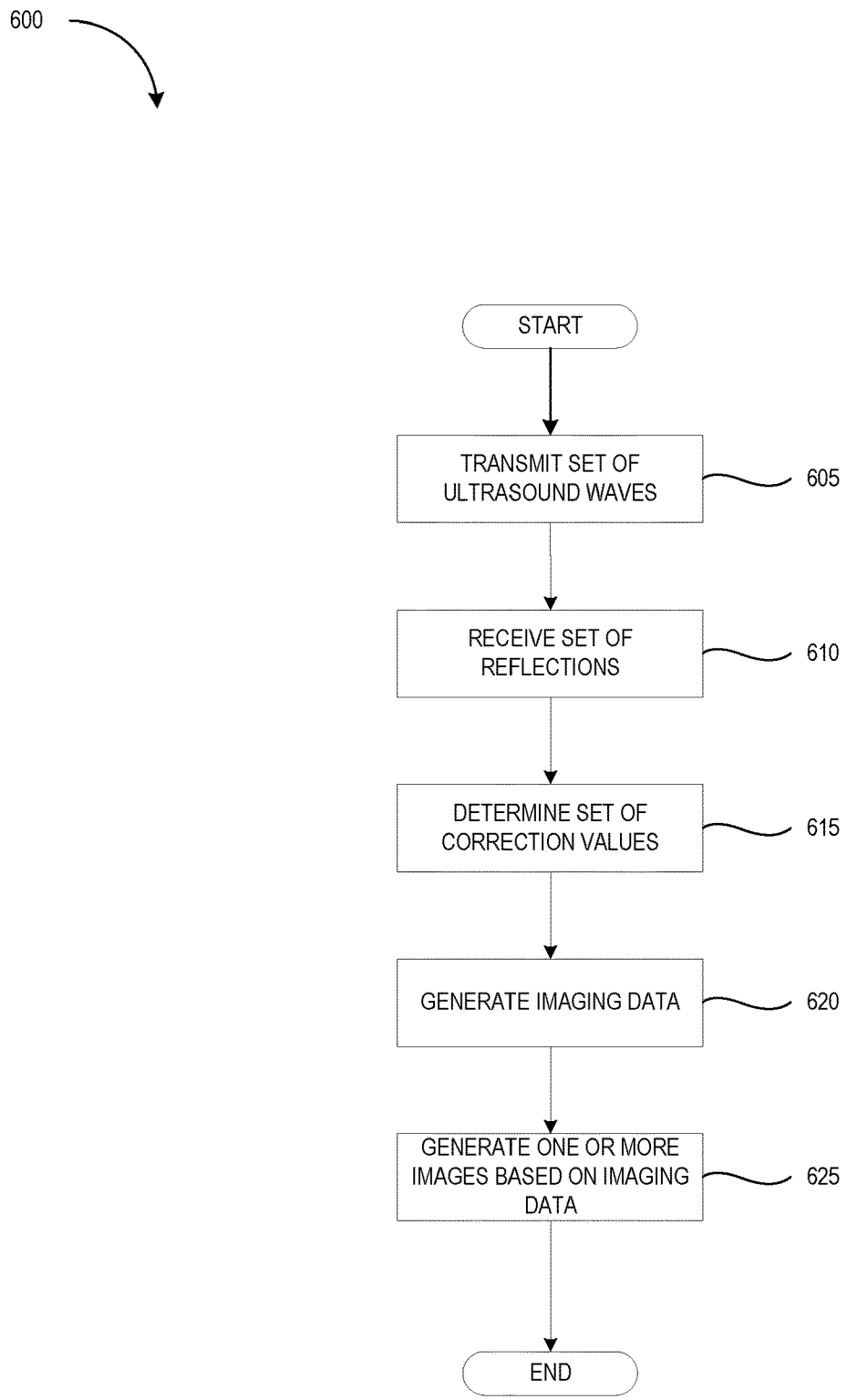
FIG. 6 is a flow diagram of a method of performing beamforming in accordance with one embodiment of the present disclosure.

FIG. 6 is a flow diagram of a method of performing beamforming in accordance with one embodiment of the present disclosure. Process 600 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the process 600 may be performed by one or more of a beamforming component, a delay component, a correction component, an ultrasound probe, an ultrasound imaging system, and/or a computing device.

The process 600 begins at block 605, where the process 600 transmits a set of ultrasound waves. For example, one or more transducer elements of the ultrasound probe may transmit, generate, emit, etc., ultrasound waves. At block 619, the process 600 may receive one or more reflections of the ultrasound waves (e.g., may receive one or more reflected ultrasound waves).

At block 615, the process 600 may generate one or more correction values. As discussed above, the one or more correction values may be delays or times that should be used when combining the imaging data (e.g., signals) from different transducer elements to perform beamforming. The correction values may be used to account for refractions as the reflected ultrasound waves pass through a transducer element. The correction values may be based on one or more of the angle of at which the ultrasound waves were transmitted, the location of a transducer element, the type of operation or procedure being performed, etc. The set of correction values may be determined by generating one or more curves (e.g., one or more piecewise linear curves), as discussed above. The one or more curves may be generated by generating portions (e.g., segments) of the curves and combining the portions of the curves.

At block 620, the process 600 may generate imaging data (e.g., signals) based on the set of correction values. For example, the process 600 may modify the signals generated by the transducer elements based on the correction values. At block 625, the process 600 may optionally generate one or more images of the target area based on the imaging data. For example, the process 600 may generate an image and display the image to a user (e.g., a doctor, clinician, technician, etc.) via a display.

Figure 7:
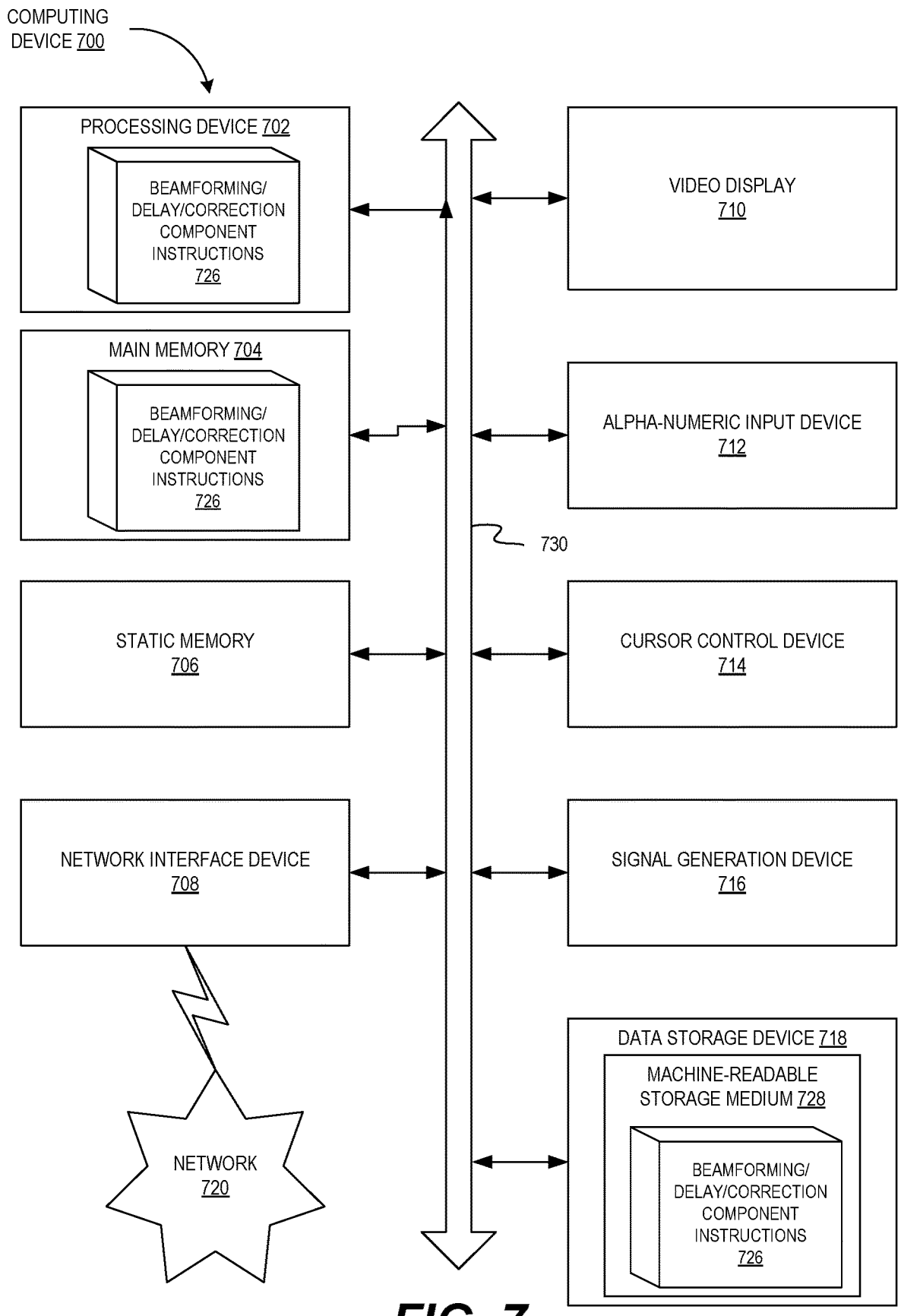
FIG. 7 is a block diagram of an example computing device that may perform one or more of the operations described herein, in accordance with one embodiment of the present disclosure.

FIG. 7 is a block diagram of an example computing device 700 that may perform one or more of the operations described herein, in accordance with some embodiments. Computing device 700 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a server computing, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some embodiments, the computing device 700 may be one or more of an access point and a packet forwarding component.

The example computing device 700 may include a processing device (e.g., a general purpose processor, a PLD, etc.) 702, a main memory 704 (e.g., synchronous dynamic random access memory (DRAM), read-only memory (ROM)), a static memory 706 (e.g., flash memory and a data storage device 718), which may communicate with each other via a bus 730.

Processing device 702 may be provided by one or more general-purpose processing devices such as a microprocessor, central processing unit, or the like. In an illustrative example, processing device 702 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 702 may also comprise one or more special-purpose processing devices such as an application specific integrated circuit (ASIC), a field programmable gate array (FPGA), a digital signal processor (DSP), network processor, or the like. The processing device 702 may be configured to execute the operations described herein, in accordance with one or more aspects of the present disclosure, for performing the operations and steps discussed herein.

Computing device 700 may further include a network interface device 708 which may communicate with a network 720. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse) and an acoustic signal generation device 716 (e.g., a speaker). In one embodiment, video display unit 710, alphanumeric input device 712, and cursor control device 714 may be combined into a single component or device (e.g., an LCD touch screen).

Data storage device 718 may include a computer-readable storage medium 728 on which may be stored one or more sets of instructions, e.g., instructions for carrying out the operations described herein, in accordance with one or more aspects of the present disclosure. Instructions 726 implementing one or more of a beamforming component, a delay component, and a correction component, may also reside, completely or at least partially, within main memory 704 and/or within processing device 702 during execution thereof by computing device 700, main memory 704 and processing device 702 also constituting computer-readable media. The instructions may further be transmitted or received over a network 720 via network interface device 708.

While computer-readable storage medium 728 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

Unless specifically stated otherwise, terms such as "transmitting," "determining," "receiving," "generating," "combining," "beamforming," or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general purpose computing device selectively programmed by a computer program stored in the computing device. Such a computer program may be stored in a computer-readable non-transitory storage medium.

The methods and illustrative examples described herein are not inherently related to any particular computer or other apparatus. Various general purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component. Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A method, comprising:
    transmitting a set of ultrasound waves to towards a target area, wherein:
        the set of ultrasound waves are transmitted by a set of ultrasound elements; and
        the set of ultrasound elements are positioned at different locations in a transducer assembly;
    receiving a set of reflections of the set of ultrasound waves from the target area, wherein the set of reflections of the set of ultrasound waves are received by the set of ultrasound elements;
    determining a set of correction values for the set of ultrasound elements,
    wherein a correction value of the set of correction values represents a refraction of a reflection of the set of reflections as the reflection passes through a lens of a first ultrasound element of the set of ultrasound elements,
    wherein at least one correction value of the set of correction values is based on a first angle of transmission of the set of ultrasound waves towards the target area and a depth of the target area relative to a skin surface; and
    generating imaging data based on the set of reflections of the set of ultrasound waves and the set of correction values for the set of ultrasound elements, wherein the correction value of the set of correction values is greater for a near field imaging of the target area than for a far field imaging of the target area, wherein the near field imaging of the target area has the depth that is smaller than the depth of the far field imaging of the target area.

2. The method of claim 1, wherein determining the set of correction values for the set of ultrasound elements comprises:
    selecting a first curve from a memory based on the first angle of transmission of the set of ultrasound waves towards the target area, the first curve representing the correction value for a first path of the reflection of the set of reflections through the lens of the first ultrasound element of the transducer assembly as a function of the depth of the target area relative to the skin surface; and
    selecting a second curve from the memory based on a second angle of transmission of the set of ultrasound waves towards the target area, the second curve representing the correction value for a second path of the reflection of the set of reflections through the lens of a second ultrasound element as a function of the depth of the target area relative to the skin surface.

3. The method of claim 2, wherein the first curve comprises a piecewise linear curve.

4. The method of claim 1, further comprising:
determining a first portion of a first curve that is stored in a memory and represents the correction value for a first path of the reflection of the set of reflections through the lens of the first ultrasound element as a function of depth of the target area;
determining a second portion of the first curve; and
combining the first portion of the first curve with the second portion of the first curve.

5. The method of claim 4, wherein the first portion of the first curve and the second portion of the first curve are determined using a first circuit.

6. The method of claim 4, wherein:
the first portion of the first curve is determined using a first circuit; and
the second portion of the first curve is determined using a second circuit.

7. The method of claim 1, wherein the correction value of the set of correction values is based on a location of the first ultrasound element within the transducer assembly.

8. The method of claim 1, wherein:
the imaging data comprises a set of signals generated by the set of ultrasound elements; and
the set of correction values comprises a set of delays for the set of signals generated by the set of ultrasound elements.

9. The method of claim 1, wherein the set of correction values is determined while a transducer probe is in operation.

10. An ultrasound probe, comprising:
a transducer assembly; and
a processing device coupled to the transducer assembly, the processing device configured to:
transmit a set of ultrasound waves to towards a target area, wherein:
the set of ultrasound waves are transmitted by a set of ultrasound elements; and
the set of ultrasound elements are positioned at different locations in the transducer assembly;
receive a set of reflections of the set of ultrasound waves from the target area, wherein the set of reflections of the set of ultrasound waves are received by the set of ultrasound elements;
determine a set of correction values for the set of ultrasound elements,
wherein a correction value of the set of correction values represents a refraction of a reflection of the set of reflections as the reflection passes through a lens of a first ultrasound element of the set of ultrasound elements,
wherein at least one correction value of the set of correction values is based on a first angle of transmission of the set of ultrasound waves towards the target area and a depth of the target area relative to a skin surface; and
generate imaging data based on the set of reflections of the set of ultrasound waves and the set of correction values for the set of ultrasound elements, wherein the correction value of the set of correction values is greater for a near field imaging of the target area than for a far field imaging of the target area, wherein the near field imaging of the target area has the depth that is smaller than the depth of the far field imaging of the target area.

11. The ultrasound probe of claim 10, wherein the correction value of the set of correction values is based on a location of the first ultrasound element within the transducer assembly.

12. The ultrasound probe of claim 10, wherein to determine the set of correction values for the set of ultrasound elements the processing device is further configured to:
select a first curve from a memory based on the first angle of transmission of the set of ultrasound waves towards the target area, the first curve representing the correction value for a first path of the reflection of the set of reflections through the lens of the first ultrasound element of the transducer assembly as a function of the depth of the target area relative to the skin surface; and
select a second curve from the memory based on a second angle of transmission of the set of ultrasound waves towards the target area, the second curve representing the correction value for a second path of the reflection of the set of reflections through the lens of a second ultrasound element as a function of the depth of the target area relative to the skin surface.

13. The ultrasound probe of claim 12, wherein the first curve comprises a piecewise linear curve.

14. The ultrasound probe of claim 10, wherein the processing device is further configured to:
determine a first portion of a first curve that is stored in a memory and represents the correction value for a first path of the reflection of the set of reflections through the lens of the first ultrasound element as a function of depth of the target area;
determine a second portion of the first curve; and
combine the first portion of the first curve with the second portion of the first curve.

15. The ultrasound probe of claim 14, wherein the first portion of the first curve and the second portion of the first curve are determined using a first circuit.

16. The ultrasound probe of claim 14, wherein:
the first portion of the first curve is determined using a first circuit; and
the second portion of the first curve is determined using a second circuit.

17. The ultrasound probe of claim 10, wherein:
the imaging data comprises a set of signals generated by the set of ultrasound elements; and
the set of correction values comprises a set of delays for the set of signals generated by the set of ultrasound elements.

18. An ultrasound imaging system, comprising:
an ultrasound probe configured to:
transmit a set of ultrasound waves to towards a target area, wherein:
the set of ultrasound waves are transmitted by a set of ultrasound elements; and
the set of ultrasound elements are positioned at different locations in a transducer assembly;
receive a set of reflections of the set of ultrasound waves from the target area, wherein the set of reflections of the set of ultrasound waves are received by the set of ultrasound elements;
determine a set of correction values for the set of ultrasound elements,
wherein a correction value of the set of correction values represents a refraction of a reflection of the set of reflections as the reflection passes through a lens of a first ultrasound element of the set of ultrasound elements, wherein at least one correction value of the set of correction values is based on a first angle of transmission of the set of ultrasound waves towards the target area and a depth of the target area relative to a skin surface, and generate imaging data based on the set of reflections of the set of ultrasound waves and the set of correction values for the set of ultrasound elements, wherein the correction value of the set of correction values is greater for a near field imaging of the target area than for a far field imaging of the target area, wherein the near field imaging of the target area has the depth that is smaller than the depth of the far field imaging of the target area; and an imaging subsystem coupled to the ultrasound probe, the imaging subsystem configured to generate one or more images of the target area based on the imaging data.

* * * * *